(12) United States Patent
Sirhan et al.

(10) Patent No.: US 6,939,375 B2
(45) Date of Patent: Sep. 6, 2005

(54) APPARATUS AND METHODS FOR CONTROLLED SUBSTANCE DELIVERY FROM IMPLANTED PROSTHESES

(75) Inventors: Motasim Sirhan, Sunnyvale, CA (US); John Yan, Los Gatos, CA (US)

(73) Assignee: Avantac Vascular Corporation, Sunnyvale, CA (US)

( * ) Notice: Subject to any disclaimer, the term of this patent is extended or adjusted under 35 U.S.C. 154(b) by 191 days.

(21) Appl. No.: 09/783,253

(22) Filed: Feb. 13, 2001

(65) Prior Publication Data

US 2002/0082685 A1 Jun. 27, 2002

Related U.S. Application Data

(60) Provisional application No. 60/258,024, filed on Dec. 22, 2000.

(51) Int. Cl.[7] .................................................. A61P 2/06
(52) U.S. Cl. ...................................... 623/1.42; 623/1.43
(58) Field of Search ............................... 623/1.39–1.48

(56) References Cited

U.S. PATENT DOCUMENTS

| | | |
|---|---|---|
| 3,976,071 A | 8/1976 | Sadek |
| 4,335,094 A | 6/1982 | Mosbach |
| 4,345,588 A | 8/1982 | Widder et al. |
| 4,357,259 A | 11/1982 | Senyei et al. |
| 4,501,726 A | 2/1985 | Schröder et al. |
| 4,810,524 A | 3/1989 | Nakayama et al. |
| 4,832,686 A | 5/1989 | Anderson |
| 4,871,716 A | 10/1989 | Longo et al. |
| 4,883,666 A | 11/1989 | Sabel et al. |
| 4,894,231 A | 1/1990 | Mareau et al. |
| 4,897,268 A | 1/1990 | Tice et al. |
| 4,904,479 A | 2/1990 | Illum |
| 4,921,723 A | 5/1990 | Nichols et al. |
| 4,936,281 A | 6/1990 | Stasz |
| 5,000,185 A | 3/1991 | Yock |
| 5,024,671 A | 6/1991 | Tu et al. |
| 5,067,491 A | 11/1991 | Taylor, II et al. |
| 5,069,216 A | 12/1991 | Groman et al. |
| 5,112,457 A | 5/1992 | Marchant |
| 5,163,952 A | 11/1992 | Froix |
| 5,176,907 A | 1/1993 | Leong |
| 5,206,159 A | 4/1993 | Cohen et al. |

(Continued)

FOREIGN PATENT DOCUMENTS

| | | |
|---|---|---|
| EP | 063 365 B1 | 9/1985 |
| EP | 184 162 B1 | 4/1994 |

(Continued)

OTHER PUBLICATIONS

Rajasubramanian et al., "Fabrication of resorbable microporous intravasular stents for gene therapy applications" *ASAIO Journal*, 40:M584–589 (1994).

(Continued)

*Primary Examiner*—Corrine McDermott
*Assistant Examiner*—Hieu Phan
(74) *Attorney, Agent, or Firm*—Townsend and Townsend and Crew LLP

(57) ABSTRACT

The present invention provides improved devices and methods for inhibiting restenosis and hyperplasia after intravascular intervention. In particular, the present invention provides luminal prostheses which allow for programmed and controlled substance delivery with increased efficacy to selected locations within a patient's vasculature to inhibit restenosis. The luminal delivery prosthesis comprises a scaffold which is implantable within a body lumen and means on the scaffold for releasing a substance from the scaffold. The substance is released over a predetermined time pattern comprising an initial phase wherein the substance delivery rate is below a threshold level and a subsequent phase wherein the substance delivery rate is above a threshold level.

16 Claims, 7 Drawing Sheets

U.S. PATENT DOCUMENTS

| | | |
|---|---|---|
| 5,225,282 A | 7/1993 | Chagnon et al. |
| 5,283,257 A | 2/1994 | Gregory et al. |
| 5,286,254 A | 2/1994 | Shapland et al. |
| 5,342,348 A | 8/1994 | Kaplan |
| 5,355,832 A | 10/1994 | Loh et al. |
| 5,356,433 A | 10/1994 | Rowland et al. |
| 5,368,557 A | 11/1994 | Nita et al. |
| 5,409,000 A | 4/1995 | Imran |
| 5,411,550 A | 5/1995 | Herweck et al. |
| 5,419,760 A | 5/1995 | Narciso, Jr. |
| 5,447,724 A | 9/1995 | Helmus et al. |
| 5,447,799 A | 9/1995 | Loh et al. |
| 5,463,010 A | 10/1995 | Hu et al. |
| 5,464,450 A | 11/1995 | Buscemi et al. |
| 5,464,650 A | 11/1995 | Berg et al. |
| 5,474,563 A | 12/1995 | Myler et al. |
| 5,484,584 A | 1/1996 | Wallace et al. |
| 5,500,013 A | 3/1996 | Buscemi et al. |
| 5,512,055 A | 4/1996 | Domb et al. |
| 5,516,781 A | 5/1996 | Morris et al. |
| 5,543,158 A | 8/1996 | Gref et al. |
| 5,545,208 A | 8/1996 | Wolff et al. |
| 5,551,954 A | 9/1996 | Buscemi et al. |
| 5,563,146 A | 10/1996 | Morris et al. |
| 5,569,463 A | 10/1996 | Helmus et al. |
| 5,591,227 A | 1/1997 | Dinh et al. |
| 5,609,629 A | 3/1997 | Fearnot et al. |
| 5,624,411 A | 4/1997 | Tuch |
| 5,637,113 A | 6/1997 | Tartaglia et al. |
| 5,646,160 A | 7/1997 | Morris et al. |
| 5,649,977 A | 7/1997 | Campbell |
| 5,656,297 A | 8/1997 | Bernstein et al. |
| 5,665,728 A | 9/1997 | Morris et al. |
| 5,679,400 A | 10/1997 | Tuch |
| 5,700,286 A | 12/1997 | Tartaglia et al. |
| 5,725,494 A | 3/1998 | Brisken |
| 5,725,567 A | 3/1998 | Wolff et al. |
| 5,728,062 A | 3/1998 | Brisken |
| 5,735,811 A | 4/1998 | Brisken |
| 5,769,883 A | 6/1998 | Buscemi et al. |
| 5,769,884 A | 6/1998 | Solovay |
| 5,824,049 A | 10/1998 | Ragheb et al. |
| 5,837,008 A | 11/1998 | Berg et al. |
| 5,843,172 A | 12/1998 | Yan |
| 5,851,231 A | 12/1998 | Wolff et al. |
| 5,876,452 A | 3/1999 | Athanasiou et al. |
| 5,879,808 A | 3/1999 | Wary et al. |
| 5,891,108 A | 4/1999 | Leone et al. |
| 5,893,840 A | 4/1999 | Hull et al. |
| 5,928,145 A | 7/1999 | Ocali et al. |
| 5,951,586 A | 9/1999 | Berg et al. |
| 5,958,510 A | 9/1999 | Sivaramakrishnam et al. |
| 5,968,092 A | 10/1999 | Buscemi et al. |
| 5,972,027 A | 10/1999 | Johnson |
| 5,980,551 A | 11/1999 | Summers et al. |
| 5,980,566 A | 11/1999 | Alt et al. |
| 5,997,468 A | 12/1999 | Wolff et al. |
| 6,031,375 A | 2/2000 | Atalar et al. |
| 6,051,276 A | 4/2000 | Wary et al. |
| 6,054,122 A | 4/2000 | MacPhee et al. |
| 6,063,101 A | 5/2000 | Jacobsen et al. |
| 6,071,305 A | 6/2000 | Brown et al. |
| 6,086,952 A | 7/2000 | Lang et al. |
| 6,096,070 A | 8/2000 | Ragheb et al. |
| 6,099,561 A | 8/2000 | Alt |
| 6,153,252 A | 11/2000 | Hossainy et al. |
| 6,183,507 B1 | 2/2001 | Lashinski et al. |
| 6,197,013 B1 | 3/2001 | Reed et al. |
| 6,203,536 B1 | 3/2001 | Berg et al. |
| 6,240,616 B1 * | 6/2001 | Yan .......................... 29/527.2 |
| 6,253,443 B1 | 7/2001 | Johnson |
| 6,273,908 B1 | 8/2001 | Ndondo-Lay |
| 6,273,913 B1 | 8/2001 | Wright et al. |
| 6,287,628 B1 | 9/2001 | Hossainy et al. |
| 6,299,604 B1 * | 10/2001 | Ragheb et al. .............. 604/265 |
| 6,395,326 B1 | 5/2002 | Castro et al. |
| 6,471,980 B2 * | 10/2002 | Sirhan et al. ................ 424/423 |
| 2001/0027340 A1 | 10/2001 | Wright et al. |
| 2001/0029351 A1 | 10/2001 | Falotico et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0016625 A1 | 2/2002 | Falotico et al. |
| 2002/0032414 A1 | 3/2002 | Ragheb et al. |

FOREIGN PATENT DOCUMENTS

| | | | |
|---|---|---|---|
| EP | 0950386 A3 | 10/1999 | |
| EP | 0950386 A2 | 10/1999 | |
| EP | 1277449 A | 1/2003 | |
| WO | WO 90/13332 | 11/1990 | |
| WO | WO 01/01957 | 1/2001 | |
| WO | WO 01/41678 | 6/2001 | ............. A61F/2/06 |
| WO | WO 02/083039 A | 10/2002 | |

OTHER PUBLICATIONS

U.S. Appl. No. 09/782,927, filed Feb. 13, 2001, entitled "Intravascular delivery of mycophenolic acid".

U.S. Appl. No. 09/783,254, filed Feb. 13, 2001, entitled Intravascular delivery of mizorbine.

U.S. Appl. No. 09/782,804, filed Feb. 13, 2001, entitled Intravascular delivery of methylprednisolone.

* cited by examiner

APPARATUS AND METHODS FOR CONTROLLED SUBSTANCE DELIVERY FROM IMPLANTED PROSTHESES

CROSS-REFERENCES TO RELATED APPLICATIONS

This application claims the benefit of Provisional Application No. 60/258,024, filed Dec. 22, 2000, under 37 C.F.R. §1.78(a)(3), the full disclosure of which is incorporated herein by reference.

BACKGROUND OF THE INVENTION

1. Field of the Invention

The present invention relates generally to medical devices and methods. More particularly, the present invention provides luminal prostheses, such as vascular stents and grafts, which allow for controlled substance delivery for inhibiting restenosis in a blood vessel following balloon angioplasty or other interventional treatments.

A number of percutaneous intravascular procedures have been developed for treating stenotic atherosclerotic regions of a patient's vasculature to restore adequate blood flow. The most successful of these treatments is percutaneous transluminal angioplasty (PTA). In PTA, a catheter, having an expansible distal end usually in the form of an inflatable balloon, is positioned in the blood vessel at the stenotic site. The expansible end is expanded to dilate the vessel to restore adequate blood flow beyond the diseased region. Other procedures for opening stenotic regions include directional arthrectomy, rotational arthrectomy, laser angioplasty, stenting, and the like. While these procedures have gained wide acceptance (either alone or in combination, particularly PTA in combination with stenting), they continue to suffer from significant disadvantages. A particularly common disadvantage with PTA and other known procedures for opening stenotic regions is the frequent occurrence of restenosis.

Restenosis refers to the re-narrowing of an artery after an initially successful angioplasty. Restenosis afflicts approximately up to 50% of all angioplasty patients and is the result of injury to the blood vessel wall during the lumen opening angioplasty procedure. In some patients, the injury initiates a repair response that is characterized by smooth muscle cell proliferation referred to as "hyperplasia" in the region traumatized by the angioplasty. This proliferation of smooth muscle cells re-narrows the lumen that was opened by the angioplasty within a few weeks to a few months, thereby necessitating a repeat PTA or other procedure to alleviate the restenosis.

A number of strategies have been proposed to treat hyperplasia and reduce restenosis. Previously proposed strategies include prolonged balloon inflation during angioplasty, treatment of the blood vessel with a heated balloon, treatment of the blood vessel with radiation following angioplasty, stenting of the region, and other procedures. While these proposals have enjoyed varying levels of success, no one of these procedures is proven to be entirely successful in completely avoiding all occurrences of restenosis and hyperplasia.

As an alternative or adjunctive to the above mentioned therapies, the administration of therapeutic agents following PTA for the inhibition of restenosis has also been proposed. Therapeutic treatments usually entail pushing or releasing a drug through a catheter or from a stent. Of particular interest herein, stents may incorporate a biodegradable or nondegradable matrix to provide programmed or controlled release of therapeutic agents within a blood vessel. Biodegradable or bioerodible matrix materials employed for controlled release of drugs may include poly-l-lactic acid/poly-e-caprolactone copolymer, polyanhydrides, polyorthoesters, polycaprolactone, poly vinly acetate, polyhydroxybutyrate/polyhyroxyvalerate copolymer, polyglycolic acid, polyactic/polyglycolic acid copolymers and other aliphatic polyesters, among a wide variety of polymeric substrates employed for this purpose.

While holding great promise, the delivery of therapeutic agents for the inhibition of restenosis has not been entirely successful. In particular, the release of drugs from stents has often been characterized by inconsistent and/or ineffective results because therapeutic agents are often released before they are needed, i.e., before hyperplasia and endothelialization begin. Drug delivery before any cellular or endothelial formation may also pose serious dangers, especially when dealing with the delivery of certain toxic agents. Furthermore, a rapid initial release of drugs causes delayed endothelialization and/or enlargement of the vessel wall, as a substantial number of cells are killed with increased drug loading. The use of drug release matrices can ameliorate the rapid release problems but do not provide programmed time-delay to impact restenosis at the onset of hyperplasia.

For these reasons, it would be desirable to provide improved devices and methods for reducing and/or inhibiting restenosis and hyperplasia following angioplasty and other interventional treatments. In particular, it would be desirable to provide improved devices and methods, utilizing luminal prostheses, such as vascular stents and grafts, which provide programmed and controlled substance delivery with increased efficacy to inhibit restenosis. It would further be desirable to provide such devices and methods which would reduce and/or further eliminate drug washout and potentially provide minimal to no hindrance to endothelialization of the vessel wall. At least some of these objectives will be met by the devices and methods of the present invention described hereinafter.

2. Description of the Background Art

A full description of an exemplary luminal prosthesis for use in the present invention is described in co-pending application Ser. No. 09/565,560 filed May 4, 2000, the full disclosure of which is incorporated herein by reference. Method and apparatus for releasing active substances from implantable and other devices are described in U.S. Pat. Nos. 6,096,070; 5,824,049; 5,624,411; 5,609,629; 5,569,463; 5,447,724; and 5,464,650. The use of stents for drug delivery within the vasculature are described in PCT Publication No. WO 01/01957 and U.S. Pat. Nos. 6,099,561; 6,071,305; 6,063,101; 5,997,468; 5,980,551; 5,980,566; 5,972,027; 5,968,092; 5,951,586; 5,893,840; 5,891,108; 5,851,231; 5,843,172; 5,837,008; 5,769,883; 5,735,811; 5,700,286; 5,679,400; 5,649,977; 5,637,113; 5,591,227; 5,551,954; 5,545,208; 5,500,013; 5,464,450; 5,419,760; 5,411,550; 5,342,348; 5,286,254; and 5,163,952. Biodegradable materials are described in U.S. Pat. Nos. 6,051,276; 5,879,808; 5,876,452; 5,656,297; 5,543,158; 5,484,584; 5,176,907; 4,894,231; 4,897,268; 4,883,666; 4,832,686; and 3,976,071. The use of hydrocylosiloxane as a rate limiting barrier is described in U.S. Pat. No. 5,463,010. Methods for coating of stents is described in U.S. Pat. No. 5,356,433. Coatings to enhance biocompatibility of implantable devices are described in U.S. Pat. Nos. 5,463,010; 5,112,457; and 5,067,491. Energy based devices are described in U.S. Pat. Nos. 6,031,375; 5,928,145; 5,735,811; 5,728,062; 5,725,494; 5,409,000, 5,368,557; 5,000,185; and 4,936,281. Magnetic processes, some of which have been used in drug delivery systems, are described in U.S. Pat. Nos. 5,427,767; 5,225,282; 25 5,206,159; 5,069,216; 4,904,479; 4,871,716; 4,501,726; 4,357,259; 4,345,588; and 4,335,094.

The disclosure of this application is related to the disclosures of the following applications being filed on the same day: Ser. No. 09/782,927; Ser. No. 09/783,254; and Ser. No. 09/782,804.

The full disclosures of each of the above references are incorporated herein by reference.

SUMMARY OF THE INVENTION

The present invention provides improved devices and methods for inhibiting restenosis and hyperplasia after intravascular intervention. In particular, the present invention provides luminal prostheses which allow for programmed and controlled substance delivery with increased efficiency and/or efficacy to selected locations within a patient's vasculature to inhibit restenosis. Moreover, the present invention minimizes drug washout and provides minimal to no hindrance to endothelialization of the vessel wall.

The term "intravascular intervention" includes a variety of corrective procedures that may be performed to at least partially resolve a stenotic, restenotic, or thrombotic condition in a body lumen. Usually, the corrective procedure will comprise balloon angioplasty. The corrective procedure could also comprise directional atherectomy, rotational atherectomy, laser angioplasty, stenting, or the like, where the lumen of the treated blood vessel is enlarged to at least partially alleviate a stenotic condition which existed prior to the treatment.

In a first aspect of the present invention, a luminal delivery prosthesis comprises a scaffold which is implantable in a body lumen and means on the scaffold for releasing a substance. The substance is released over a predetermined time pattern comprising an initial phase wherein the substance delivery rate is below a threshold level and a subsequent phase wherein the substance delivery rate is above a threshold level.

The predetermined time pattern of the present invention improves the efficiency of drug delivery by releasing a lower or minimal amount of the substance until a subsequent phase is reached, at which point the release of the substance may be substantially higher. Thus, time delayed substance release can be programmed to impact restenosis substantially at the onset of events leading to smooth muscle cell proliferation (hyperplasia), The present invention can further minimize substance washout by timing substance release to occur after at least initial cellularization and/or endothelialization which creates a barrier over the stent to reduce loss of the substance directly into the bloodstream. Moreover, the predetermined time pattern may reduce substance loading and/or substance concentration as well as potentially providing minimal to no hindrance to endothelialization of the vessel wall due to the minimization of drug washout and the increased efficiency of substance release.

The scaffold may be in the form of a stent, which additionally maintains luminal patency, or may be in the form of a graft, which additionally protects or enhances the strength of a luminal wall. The scaffold may be radially expansible and/or self-expanding and is preferably suitable for luminal placement in a body lumen. The body lumen may be any blood vessel in the patient's vasculature, including veins, arteries, aorta, and particularly including coronary and peripheral arteries, as well as previously implanted grafts, shunts, fistulas, and the like. It will be appreciated that the present invention may also be applied to other body lumens as well as to many internal corporeal tissue organs, such as organs, nerves, glands, ducts, and the like. An exemplary stent for use in the present invention is described in co-pending application ser. No. 09/565,560.

It will be appreciated that the above-described benefits of time delayed release allow for a wide array of substances to be effectively delivered. The substance may comprise at least one agent selected from the group consisting of immunosuppressant agent, anti-inflammatory agent, anti-proliferative agent, anti-migratory agent, anti-fibrotic agent, anti-thrombotic agent, anti-platelet agent, and IIb/IIIa agent. Preferably, the agent is an immunosuppressant agent selected from the group consisting of mycophenolic acid, rapamycin, cyclosporine A, cycloheximide, cyclophoshamide, mizoribine, methylprednisolone, azathioprine, ribovirin, FK506, tiazofurin, methotrexate, zafurin, and mycophenolate mofetil. The total amount of substance released will typically be in a range from 1 $\mu$g. to 2000 $\mu$g., preferably in a range from 10 $\mu$g. to 1000 $\mu$g., most preferably in a range from 50 $\mu$g. to 500 $\mu$g. The release rate during the initial phase will typically be from 0 $\mu$g/day to 50 $\mu$g/day, usually from 5 $\mu$g/day to 30 $\mu$g/day. The substance release rate during the subsequent phase will be much higher, typically being in the range from 5 $\mu$g/day to 200 $\mu$g/day, usually from 10 $\mu$g/day to 100 $\mu$g/day. Thus, the initial release rate will typically be from 0% to 99% of the subsequent release rates, usually from 0% to 90%, preferably from 0% to 75%. Of course, the release rates may vary during either or both of the initial and subsequent release phases. There may also be additional phase(s) for release of the same substance(s) and/or different substance(s).

The duration of the initial, subsequent, and any other additional phases may vary. Typically, the initial phase will be sufficiently long to allow initial cellularization or endothelialization of at least part of the stent, usually being less than 12 weeks, more usually from 1 hour to 8 weeks, more preferably from 12 hours to 2 weeks, most preferably from 1 day to 1 week. The durations of the subsequent phases may also vary, typically being from 4 hours to 24 weeks, more usually from 1 day to 12 weeks, more preferably in a time period of 2 days to 8 weeks in a vascular environment, most preferably in a time period of 3 days to 50 days in a vascular environment.

In a first embodiment, the means for releasing the substance comprises a matrix formed over at least a portion of the scaffold, wherein the matrix is composed of degradable, partially degradable, nondegradable polymer, synthetic, or natural material. The substance to be delivered may be disposed within the matrix or adjacent to the matrix in a pattern that provides the desired release rates, e.g. as dispersed particles . Alternatively, the substance may be disposed on or within the scaffold adjacent to the matrix to provide the desired release rates, e.g. as dispersed particles. Suitable biodegradable or bioerodible matrix materials include polyanhydrides, polyorthoesters, polycaprolactone, poly vinly acetate, polyhydroxybutyrate-polyhyroxyvalerate, polyglycolic acid, polyactic/polyglycolic acid copolymers and other aliphatic polyesters, among a wide variety of polymeric substrates employed for this purpose. A preferred biodegradable matrix material of the present invention is a copolymer of poly-l-lactic acid and poly-e-caprolactone. Suitable nondegradable matrix materials include polyurethane, polyethylene imine, cellulose acetate butyrate, ethylene vinyl alcohol copolymer, silicone rubber, or the like.

The polymer matrix may degrade by bulk degradation, in which the matrix degrades throughout, or preferably by surface degradation, in which a surface of the matrix degrades over time while maintaining bulk integrity. Hydrophobic matrices are preferred as they tend to release the substance over the predetermined time pattern. Alternatively, a nondegradable matrix may release the substance by diffusion.

In some instances, the matrix may comprise multiple adjacent layers of same or different matrix material, each layer containing a different, same, or no substance. For example, a first substance disposed within a top degradable layer of the matrix is released as the top matrix layer degrades and a second substance disposed within an adjacent nondegradable matrix layer is released primarily by diffusion. In some instances, multiple substances may be disposed within a single matrix layer.

Additionally, a rate limiting barrier may be formed adjacent to the scaffold and/or the matrix. Such rate limiting barriers may be nonerodible or nondegradable, such as silicone, polytetrafluorethylene (PTFE), paralene, and parylast, and control the flow rate of release passing through the rate limiting barrier. In such a case, the substance may be released by diffusion through the rate limiting barrier. Furthermore, a biocompatible or blood compatible layer, such as polyethylene glycol (PEG), may be formed over the matrix or rate limiting barrier to make the delivery prosthesis more biocompatible.

In a second embodiment, the means for releasing the substance comprises a rate limiting barrier formed over at least a portion of the scaffold. The rate limiting barrier has a sufficient thickness so that release of the substance from the barrier begins substantially after a preselected time period. Rate limiting barriers will typically have a thickness in a range from 0.01 micron to 100 microns, preferably in a range from 0.1 micron to 10 microns, to provide substantial substance release over the predetermined time pattern. The rate limiting barrier is typically nonerodible such as silicone, PTFE, parylast, polyurethane, paralene, or a combination thereof and substance release through such rate limiting barriers is usually accomplished by diffusion. In some instances, the rate limiting barrier may comprise multiple adjacent layers of same or different barrier material, each layer containing a different, same, or no substance. Multiple substances may also be contained within a single barrier layer.

In a third embodiment, the means for releasing the substance comprises a reservoir on or within the scaffold containing the substance and a cover over the reservoir.

The cover may be degradable or partially degradable over a preselected time period so that release of the substance from the reservoir begins substantially after the preselected time period. The cover may comprise a polymer matrix, as described above, which contains the substance within the reservoir. A rate limiting barrier, such as silicone, may additionally be formed adjacent to the reservoir and/or the cover, thus allowing the substance to be released by diffusion through the rate limiting barrier. Alternatively, the cover may be a nondegradable matrix or rate limiting barrier having a sufficient thickness so that release of the substance from the reservoir begins substantially after a preselected time period.

In a fourth embodiment, the means for releasing the substance comprises a reservoir on or within the scaffold containing the substance and an external energy source for directing energy at the prosthesis after implantation to effect release of the substance. A matrix or barrier may be formed adjacent to the reservoir to contain the substance within the reservoir. Alternatively, the means for releasing the substance may comprise a matrix or rate limiting barrier formed over at least a portion of the scaffold, wherein the substance is disposed adjacent or within the matrix or barrier, and an external energy source for directing energy at the prosthesis after implantation to effect release of the substance. The external energy source may comprise ultrasound, magnetic resonance imaging, magnetic field, radio frequency, temperature change, electromagnetic, x-ray, radiation, heat, gamma, or microwave. Exposure of the prosthesis to an external energy source may change a porosity, diffusion rate, hydrophilicity, or hydrophobicity of the prosthesis, thus allowing release of the substance over the predetermined time pattern.

In a fifth embodiment, the means for releasing the substance comprises magnetic particles coupled to the substance or the scaffold and a magnetic source for directing a magnetic field at the prosthesis after implantation to effect release of the substance. Optionally, the means for releasing the substance may comprise magnetic particles coupled to a matrix or barrier which may be coupled to the scaffold and a magnetic source for directing a magnetic field at the prosthesis after implantation to effect release of the substance. The substance in this later configuration may be disposed adjacent or within the matrix or barrier. The magnetic particles may be formed from magnetic beads that become activated under the direction of the magnetic field, thus effecting release of the substance according to the predetermined time pattern.

In a sixth embodiment, the means for releasing the substance comprises a change in a pH level to effect release of the substance. For instance, an inflamed restenotic region may exhibit a change in an acidic environment which may cause degradation of a matrix to effect release of the substance.

In a seventh embodiment, the means for releasing the substance comprises a reservoir on or within the scaffold containing the substance and vibrational or heating energy directed at the prosthesis after implantation to effect release of the substance. Alternatively, a matrix or rate limiting barrier formed adjacent the scaffold containing the substance may also be employed with the vibration or heat energy to effect release of the substance after prosthesis implantation.

In a second aspect of the present invention, an intraluminal delivery prosthesis of the present invention comprises a scaffold which is implantable in a body lumen and means on the scaffold for releasing two substances. The two substances are released over two predetermined time patterns comprising an initial phase wherein a substance delivery rate is below a threshold level and a subsequent phase wherein the substance delivery rate is above a threshold level. The means for releasing the two substances may comprise a matrix or rate limiting barrier having multiple layers formed over at least a portion of the scaffold. The two substances may be released at different time patterns, wherein a second substance is released after a threshold level of a first substance is reached. Alternatively, the two substances may be simultaneously or sequentially released.

In a third aspect of the present invention, improved methods for delivering a pharmacological agent to an artery are provided, said method being of the type where a prosthesis is implanted in the artery or vein, and the prosthesis releases the pharmacological agent. The improvement comprises implanting a prosthesis that is programmed to begin substantial release of the pharmacological agent beginning after growth of at least one layer of cells over a part of the prosthesis. The cells will generally comprise inflammatory, smooth muscle, or endothelial cells, indicating the onset of the healing process of restenosis.

In a fourth aspect of the present invention, methods for luminal substance delivery are provided. For example, one method may include providing a luminal prosthesis incorporating or coupled to the substance. The prosthesis is coated with a matrix which undergoes degradation in a vascular environment. The prosthesis is implanted in a body lumen so that at least a portion of the matrix degrades over a predetermined time period and substantial substance release begins after the matrix substantially begins to degrade. Typically, the matrix will degrade sufficiently to begin substantial release of the substance within a time period of 4 hours to 24 weeks in a vascular environment, preferably in a time period of 1 day to 12 weeks in a vascular environment, more preferably in a time period of 2 days to 8 weeks in a vascular environment, most preferably in a time period of 3 days to 50 days in a vascular environment.

The substance may be incorporated in a reservoir in or on a scaffold. In this configuration, the reservoir is covered by the matrix so that the substance release begins substantially after the matrix has degraded sufficiently to uncover the reservoir. Alternatively, the substance may be dispersed within or adjacent the matrix with the matrix coating a scaffold. In this configuration, an outer layer of the matrix is substantially free from the substance so that the substance release will not substantially begin until the outer layer has degraded, the outer layer comprising a degradable matrix material. Optionally, the substance may be dispersed within or on a scaffold coated by the matrix. The prosthesis may be coated with the matrix by spraying, dipping, deposition, or painting. Likewise, the prosthesis may incorporate the substance by coating, spraying, dipping, deposition, or painting the substance on the prosthesis.

Another method for luminal substance delivery comprises providing a luminal prosthesis incorporating or coupled to the substance. The prosthesis contains a rate limiting barrier or nondegradable matrix having a sufficient thickness to allow diffusion of the substance through the barrier or nondegradable matrix. The prosthesis is implanted in a body lumen so that substantial substance release from the barrier or nondegradable matrix begins after a preselected time period.

A further method for luminal substance delivery comprises implanting a luminal prosthesis in a lumen of a patient. The prosthesis incorporates a substance to be released into the lumen or luminal wall. Energy is then directed at the prosthesis to effect release of the substance form the prosthesis.

Yet another method for luminal substance delivery comprises implanting a device in a patient. The device incorporates magnetic particles adjacent or coupled to the substance. A magnetic field is then directed at the device to effect release of the particles from the device.

In a fifth aspect of the present invention, kits comprising a luminal prosthesis and instructions on how to implant the prosthesis for luminal substance delivery are provided. The luminal prosthesis may comprise any of the structures described herein, while instructions for luminal substance delivery will generally recite the steps for performing one or more of the above described methods. The instructions will often be printed, optionally being at least in-part disposed on packaging. The instructions may alternatively comprise a videotape, a CD-ROM or other machine readable code, a graphical representation, or the like showing any of the above described methods.

DESCRIPTION OF THE SPECIFIC EMBODIMENTS

The present invention provides improved devices and methods for inhibiting restenosis and hyperplasia after intravascular intervention. In particular, the present invention provides luminal prostheses which allow for programmed and controlled substance delivery with increased efficacy to selected locations within a patient's vasculature to inhibit restenosis.

Figure 1:
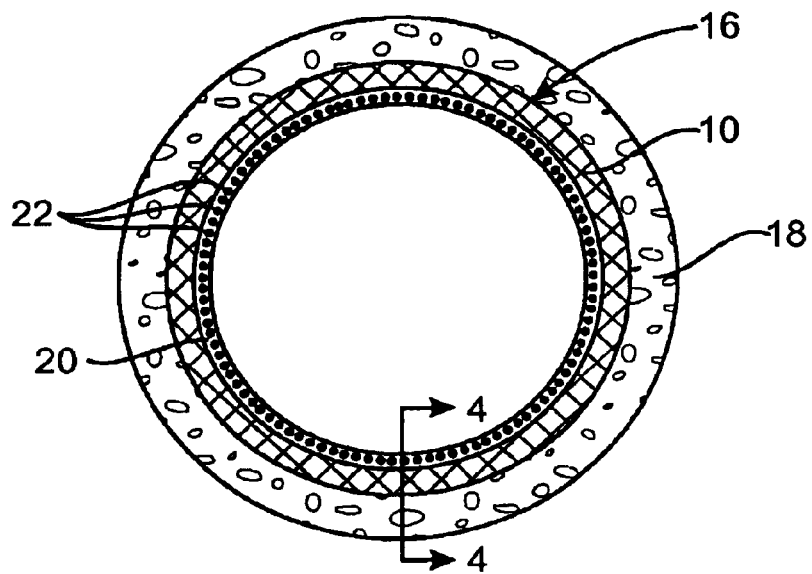
FIGS. 1 and 1A are cross-sectional views of a delivery prosthesis implanted in a body lumen.
Figure 1A:
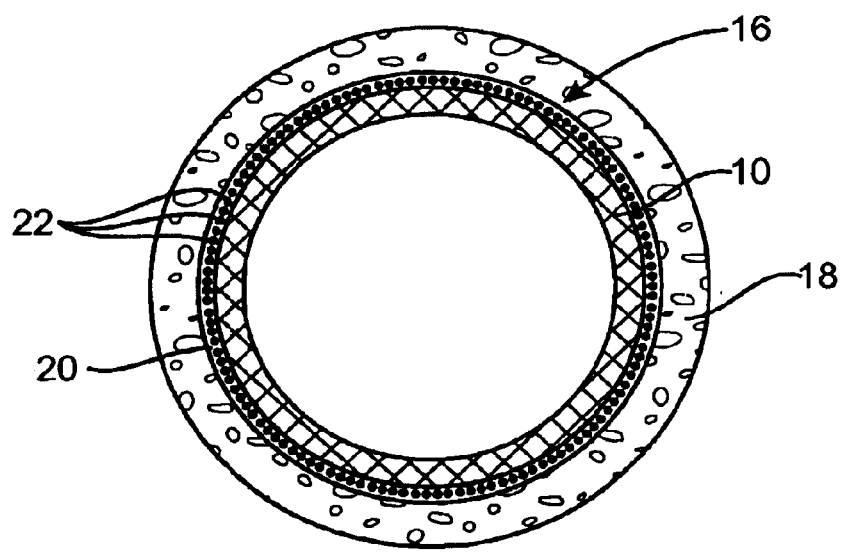

FIGS. 1 and 1A illustrate a delivery prosthesis 16 constructed in accordance with the principles of the present invention. The luminal delivery prosthesis 16 comprises a scaffold 10 which is implantable in a body lumen 18 and means 20 on the scaffold 10 for releasing a substance 22. The substance 22 is released over a predetermined time pattern comprising an initial phase wherein the substance delivery rate is below a threshold level and a subsequent phase wherein the substance delivery rate is above a threshold level.

It will be appreciated that the following depictions are for illustration purposes only and does not necessarily reflect the actual shape, size, or distribution of the delivery prosthesis 16. For example, the means or source 20 for releasing the substance (matrix, rate limiting barrier, reservoir, and other rate controlling means) may be coupled to a portion, inside, outside, or both sides of the prosthesis. The term "coupled to" includes connected to, attached to, adjacent to, and like configurations. Additionally, the substance 22 may be disposed within the means or source for releasing the substance, on or within the scaffold, or the substance may alternatively be adhering to the scaffold, bonded to the scaffold, or entrapped within the scaffold. This applies to all depictions hereinafter.

The body lumen 18 may be any blood vessel in the patient's vasculature, including veins, arteries, aorta, and particularly including coronary and peripheral arteries, as well as previously implanted grafts, shunts, fistulas, and the like. It will be appreciated that the present invention may also find use in body lumens 18 other than blood vessels. For example, the present invention may be applied to many internal corporeal tissue organs, such as organs, nerves, glands, ducts, and the like.

The scaffold 10 will comprise a stent or graft, which may be covered by one or more layer of cells. As a stent example, the scaffold 10 will usually comprise at least two radially expansible, usually cylindrical, ring segments. Typically, the scaffold 10 will have at least four, and often five, six, seven, eight, ten, or more ring segments. At least some of the ring segments will be adjacent to each other but others may be separated by other non-ring structures.

By "radially expansible," it is meant that the segment can be converted from a small diameter configuration to a radially expanded, usually cylindrical, configuration which is achieved when the scaffold 10 is implanted at a desired target site. The scaffold 10 may be minimally resilient, e.g., malleable, thus requiring the application of an internal force to expand and set it at the target site. Typically, the expansive force can be provided by a balloon, such as the balloon of an angioplasty catheter for vascular procedures. The scaffold 10 preferably provides sigmoidal links between successive unit segments which are particularly useful to enhance flexibility and crimpability of the stent.

Alternatively, the scaffold 10 can be self-expanding. Such self-expanding structures are provided by utilizing a resilient material, such as a tempered stainless steel or a superelastic alloy such as a Nitinol™ alloy, and forming the body segment so that it possesses its desired, radially-expanded diameter when it is unconstrained, i.e. released from the radially constraining forces of a sheath. In order to remain anchored in the body lumen, the scaffold 10 will remain partially constrained by the lumen. The self-expanding scaffold can be tracked and delivered in its radially constrained configuration, e.g., by placing the scaffold 10 within a delivery sheath or tube and removing the sheath at the target site.

The dimensions of the scaffold 10 will depend on its intended use. Typically, the scaffold 10 will have a length in a range from about 5 mm to 100 mm, usually being from about 8 mm to 50 mm, for vascular applications. The small (radially collapsed) diameter of cylindrical scaffold 10 will usually be in a range from about 0.5 mm to 10 mm, more usually being in a range from 0.8 mm to 8 mm for vascular applications. The expanded diameter will usually be in a range from about 1.0 mm to 100 mm, preferably being in a range from about 2.0 mm to 30 mm for vascular applications. The scaffold 10 will have a thickness in a range from 0.025 mm to 2.0 mm, preferably being in a range from 0.05 mm to 0.5 mm.

The ring segments may be formed from conventional materials used for body lumen stents and grafts, typically being formed from malleable metals, such as 300 series stainless steel, or from resilient metals, such as superelastic and shape memory alloys, e.g., Nitinol™ alloys, spring stainless steels, and the like. It is possible that the body segments could be formed from combinations of these metals, or combinations of these types of metals and other non-metallic materials. Additional structures for the body or unit segments of the present invention are illustrated in U.S. Pat. Nos. 5,195,417; 5,102,417; and 4,776,337, the full disclosures of which are incorporated herein by reference.

Figure 2:
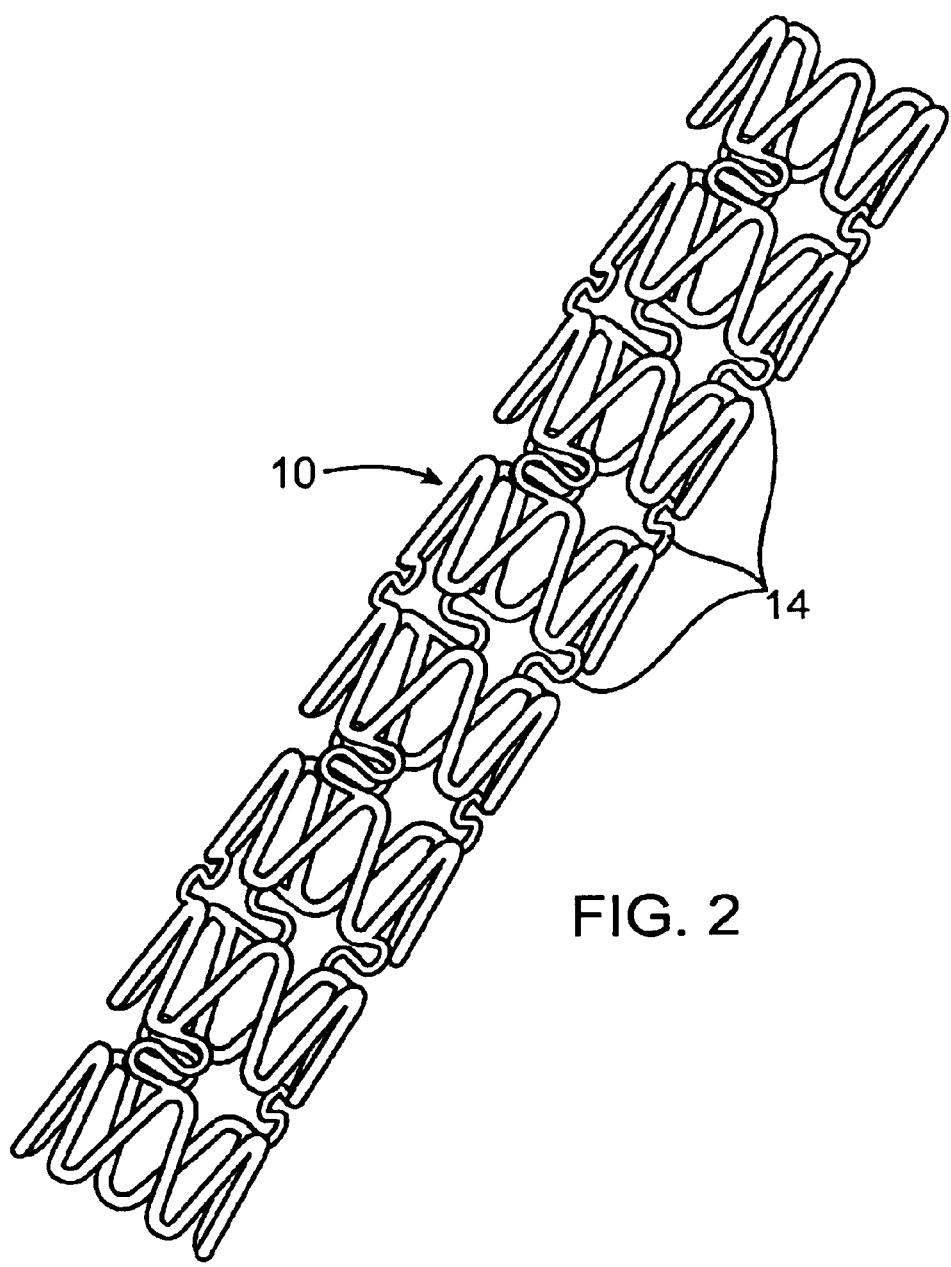
FIG. 2 is a digital photograph of an exemplary stent of the delivery prosthesis prior to expansion.

Referring now to FIG. 2, an exemplary stent 10 (which is described in more detail in co-pending application Ser. No. 09/565,560) for use in the present invention comprises from 4 to 50 ring segments 12 (with seven being illustrated). Each ring segment 12 is joined 10 to the adjacent ring segment by at least one of sigmoidal links 14 (with three being illustrated). Each ring segment 12 includes a plurality, e.g., six strut/hinge units, and two out of each six hinge/strut structures on each ring segment 12 will be joined by the sigmoidal links 14 to the adjacent ring segment. FIG. 2 shows the stent 10 in a collapsed or narrow diameter configuration.

Figure 3:
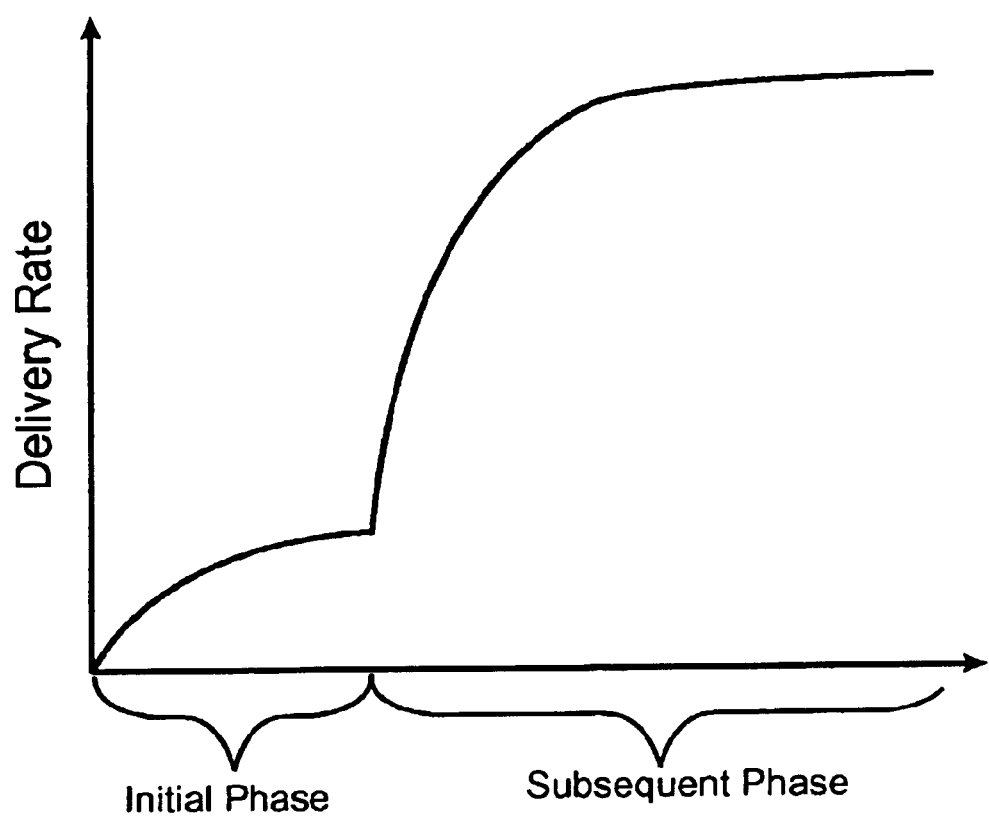
FIG. 3 is a graphical representation of substance release over a predetermined time period.

Referring now to FIG. 3, a graphical representation of substance release over a predetermined time period is illustrated. The predetermined time pattern of the present invention improves the efficiency of drug delivery by releasing the substance at a lower or minimal delivery rate during an initial phase. Once a subsequent phase is reached, the delivery rate of the substance may be substantially higher. Thus, time delayed substance release can be programmed to impact restenosis at the onset of initial cellular deposition or proliferation (hyperplasia). The present invention can further minimize substance washout by timing substance release to occur after at least initial cellularization. Moreover, the predetermined time pattern may reduce substance loading and/or substance concentration as well as potentially provide minimal to no hindrance to endothelialization of the vessel wall due to the minimization of drug washout and the increased efficiency of substance release.

A wide variety of pharmacological substances 22 may be effectively delivered in the present invention. Suitable substances 22 that may be delivered include drugs and pro-drugs (precursor substances that are converted into an active form in the body) which include immunosuppressant agents (e.g., mycophenolic acid, rapamycin, cyclosporine A, cycloheximide, cyclophosphamide, mizoribine, methylprednisolone, azathioprine, ribovirin, FK506, tiazofurin, methotrexate, zafurin, and mycophenolate mofetil), anti-inflammatory agents (e.g., thalidomide, ketoprofin, sulindae, curcumin, cortisone, corticosterone, and dexamethasone), anti-proliferative agents (e.g., chemotherapeutic and cytostatic agents), antimigratory agents (e.g., marimastat), anti-fibrotic agents (e.g., MMP inhibitors), antithrombotic agents (e.g., lytic agents, such as recombinant tissue plasminogen activator, urokinase, and streptokinase), anti-coagulant agents (e.g., heparin and low molecular weight heparins), anti-mitotics (e.g., colchicine), anti-platelet agents (e.g., ticlid, plavax), IIb/IIIa agents, and the like. The agent may also be a prodrug of any of the above listed agents. Preferably, the delivered agent is an immunosuppressant agent, more preferably the agent is mycophenolic acid or mycophenolate mofetil, alone or in combination with any of the other agents listed above. Most preferred is the use of any one of mycophenolic acid, mizoribine, and methylprednisolone, as described in application Ser. No. 09/782,927, Ser. No. 09/783,254, and Ser. No. 09/782,804, filed on the same day as the present application and incorporated herein by reference.

The agents delivered may perform a variety of functions, including preventing or minimizing proliferative/restenotic activity, inhibiting thrombus formation, inhibiting platelet activation, preventing vasospasm, or the like. The total amount of substance released depends in part on the level and amount of vessel injury, and will typically be in a range from 1 μg. to 2000 μg., preferably in a range from 10 μg. to 1000 μg. The release rate during the initial phase will typically be from 0 μg/day to 50 μg/day, usually from 5 μg/day to 30 μg/day. The substance release rate during the subsequent phase will be much higher, typically being in the range from 5 µg/day to 200 µg/day, usually from 10 µg/day to 100 µg/day. Thus, the initial release rate will typically be from 0% to 99% of the subsequent release rates, usually from 0% to 90%, preferably from 0% to 75%. A mammalian tissue concentration of the substance at an initial phase will typically be within a range from 0 µg/mg of tissue to 100 µg/mg of tissue, preferably from 0 µg/mg of tissue to 10 µg/mg of tissue. A mammalian tissue concentration of the substance at a subsequent phase will typically be within a range from 1 picogram/mg of tissue to 100 µg/mg of tissue, preferably from 1 nanogram/mg of tissue to 10 µg/mg of tissue.

The duration of the initial, subsequent, and any other additional phases may vary. Typically, the initial phase will be sufficiently long to allow initial cellularization or endothelialization of at least part of the stent, usually being less than 12 weeks, more usually from 1 hour to 8 weeks, more preferably from 12 hours to 2 weeks, most preferably from 1 day to 1 week. The durations of the subsequent phases may also vary, typically being from 4 hours to 24 weeks, more usually from 1 day to 12 weeks, more preferably in a time period of 2 days to 8 weeks in a vascular environment, most preferably in a time period of 3 days to 50 days in a vascular environment.

Figure 4:
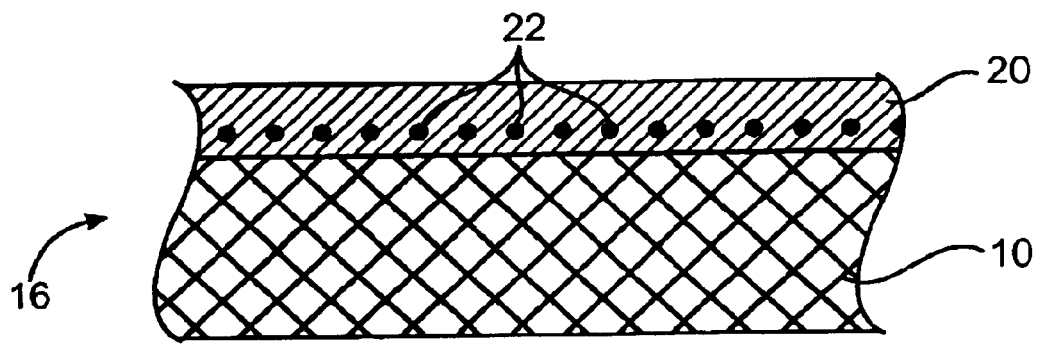
FIG. 4 is a partial cross-sectional view of a delivery prosthesis having a matrix for releasing a substance disposed within the matrix.

In one embodiment, the means for releasing the substance comprises a matrix or coat 20 formed over at least a portion of the scaffold 10, wherein the matrix 20 is composed of material which undergoes degradation. As shown in FIG. 4, the substance 22 to be delivered may be disposed within the matrix 20 in a pattern that provides the desired release rates. Alternatively, the substance 22 may be disposed within or on the scaffold 10 under the matrix 20 to provide the desired release rates, as illustrated respectively in FIGS. 5 and 6.

It will be appreciated that the scaffold 10 acts as a mechanical support for the delivery matrix 20, thus allowing a wide variety of materials to be utilized as the delivery matrix 20. Suitable biodegradable or bioerodible matrix materials include polyanhydrides, polyorthoesters, polycaprolactone, poly vinly acetate, polyhydroxybutyrate-polyhyroxyvalerate, polyglycolic acid, polyactic/ polyglycolic acid copolymers and other aliphatic polyesters, among a wide variety of synthetic or natural polymeric substrates employed for this purpose.

An example of a biodegradable matrix material of the present invention is a copolymer of poly-l-lactic acid (having an average molecular weight of about 200,000 daltons) and poly-e-caprolactone (having an average molecular weight of about 30,000 daltons). Poly-e-caprolactone (PCL) is a semi crystalline polymer with a melting point in a range from 59° C. to 64° C. and a degradation time of about 2 years. Thus, poly-l-lactic acid (PLLA) can be combined with PCL to form a matrix that generates the desired release rates. A preferred ratio of PLLA to PCL is 75:25 (PLLA/PCL). As generally described by Rajasubramanian et al. in *ASAIO Journal*, 40, pp. M584–589 (1994), the full disclosure of which is incorporated herein by reference, a 75:25 PLLA/PCL copolymer blend exhibits sufficient strength and tensile properties to allow for easier coating of the PLLA/PLA matrix on the scaffold. Additionally, a 75:25 PLLA/PCL copolymer matrix allows for controlled drug delivery over a predetermined time period as a lower PCL content makes the copolymer blend less hydrophobic while a higher PLLA content leads to reduced bulk porosity.

The polymer matrix 20 may degrade by bulk degradation, in which the matrix degrades throughout, or preferably by surface degradation, in which only a surface of the matrix degrades over time while maintaining bulk integrity. Alternatively, the matrix 20 may be composed of a nondegradable material which releases the substance by diffusion. Suitable nondegradable matrix materials include polyurethane, polyethylene imine, cellulose acetate butyrate, ethylene vinyl alcohol copolymer, or the like.

Figure 7:
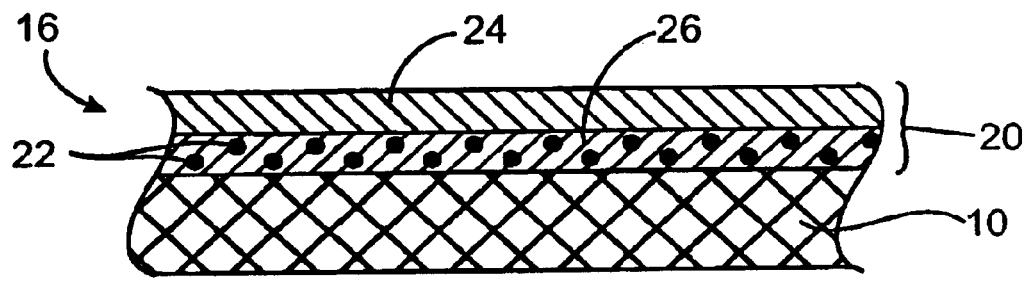
FIG. 7 is a partial cross-sectional view of a delivery prosthesis having multiple matrix layers.
Figure 8:
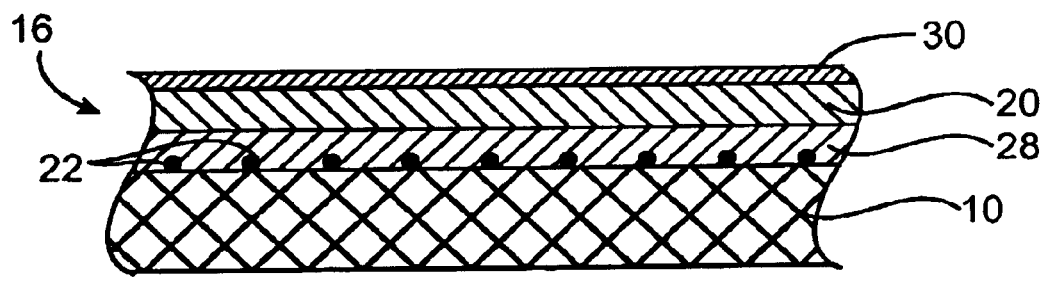
FIG. 8 is a partial cross-sectional view of a delivery prosthesis having a matrix between a rate limiting barrier and a biocompatible layer.

Referring now to FIG. 7, the matrix 20 may comprise multiple layers 24 and 26, each layer containing a different, same, or no substance. As shown, a top layer 24 may contain no substance while a bottom layer 26 contains a substance 22. As the top layer 24 degrades, the substance 22 delivery rate increases. Additionally, the present invention may employ a rate limiting barrier 28 formed between the scaffold 10 and the matrix 20, as illustrated in FIG. 8, or may optionally be formed over the matrix 20. Such rate limiting barriers 28 may be nonerodible and control the flow rate of release by diffusion of the substance 22 through the barrier 28. Suitable nonerodible rate limiting barriers 28 include silicone, PTFE, paralene, parylast, and the like. Furthermore, a layer 30, such as polyethylene glycol (PEG), and the like, may be formed over the matrix 20 to make the delivery prosthesis 16 more biocompatible.

Figure 9:
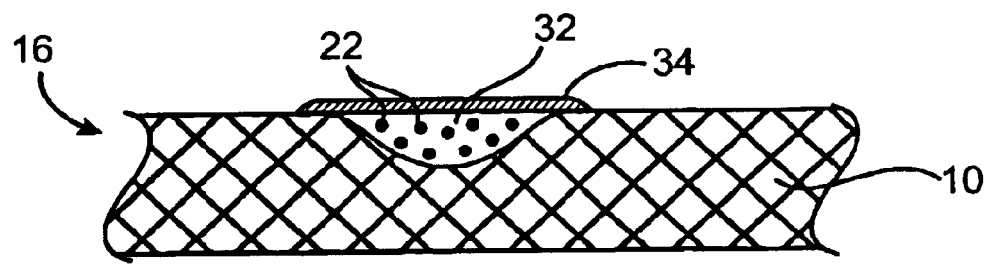
FIG. 9 is a partial cross-sectional view of a delivery prosthesis having a reservoir type releasing means.

In another embodiment, as illustrated in FIG. 9, the means for releasing the substance comprises a reservoir 32 on or within the scaffold 10 containing the substance 22 and a cover 34 over the reservoir 32. The cover 34 is degradable over a preselected time period so that release of the substance 22 from the reservoir 32 begins substantially after the preselected time period. The cover 34, in this example, may comprise a polymer matrix, as described above, which contains the substance 22 within the reservoir 32 so that the matrix 34 is replenished by the substance 22 within the reservoir 32. A rate limiting barrier 28, as described with reference to FIG. 8, may additionally be formed between the reservoir 32 and the cover 34, or on top of the cover 34, thus allowing the substance to be released by diffusion through the rate limiting barrier 28.

In operation, methods for luminal substance delivery comprise providing a luminal prosthesis incorporating or coupled to the substance. The prosthesis is coated with a matrix which undergoes degradation in a vascular environment (FIGS. 4–9). The prosthesis is implanted in a body lumen (FIGS. 12A–12C) so that at least a portion of the matrix degrades over a predetermined time period and substantial substance release begins after the portion has degraded. Optionally, the prosthesis may be coated with a rate limiting barrier or nondegradable matrix having a sufficient thickness to allow diffusion of the substance through the barrier or nondegradable matrix. The prosthesis is implanted in a body lumen so that substantial substance release from the barrier or nondegradable matrix begins after a preselected time period. As the proliferative effects of restenosis usually occur within a few weeks to a few months, substantial release of the substance will begin within a time period of 4 hours to 24 weeks in a vascular environment, preferably in a time period of 1 days to 12 weeks in a vascular environment, more preferably in a time period of 2 days to 8 weeks in a vascular environment, most preferably in a time period of 3 days to 50 days in a vascular environment.

Figure 5:
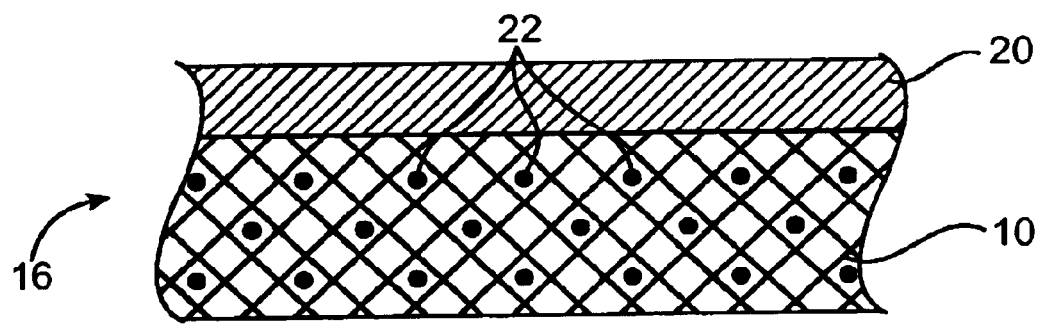
FIG. 5 is a partial cross-sectional view of a delivery prosthesis having a scaffold containing a substance.
Figure 6:
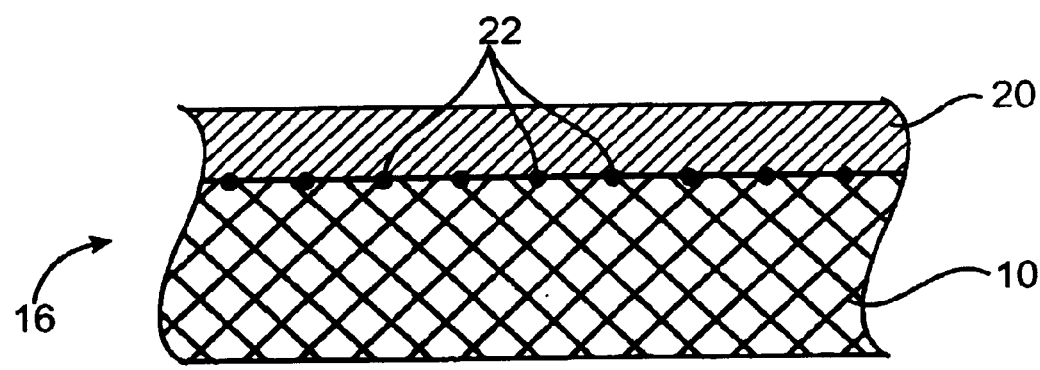
FIG. 6 is a partial cross-sectional view of a delivery prosthesis having a scaffold and a substance disposed on a scaffold surface.

The substance may be incorporated in a reservoir in a scaffold, as shown in FIG. 9, or on a scaffold. In this configuration, the reservoir is covered by the matrix so that the substance release begins substantially after the matrix has degraded sufficiently to uncover the reservoir. Alternatively, the substance may be dispersed in the matrix with the matrix coating a scaffold (FIG. 7). In this configuration, an outer layer of the matrix is substantially free from the substance so that the substance release will not substantially begin until the outer layer has degraded. Optionally, the substance may be dispersed within or on a scaffold coated by the matrix (FIGS. 5–6).

The prosthesis 16 may incorporate the substance 22 by coating, spraying, dipping, deposition, or painting the substance on the prosthesis. Usually, the substance 22 is dissolved in a solvent to make a solution. Suitable solvents include aqueous solvents (e.g., water with pH buffers, pH adjusters, organic salts, and inorganic salts), alcohols (e.g., methanol, ethanol, propanol, isopropanol, hexanol, and glycols), nitrites (e.g., acetonitrile, benzonitrile, and butyronitrile), amides (e.g., formamide and N dimethylformamide), ketones, esters, ethers, DMSO, gases (e.g., $CO_2$), and the like. For example, the prosthesis may be sprayed with or dipped in the solution and dried so that the substance crystals are left on a surface of the prosthesis. Alternatively, the prosthesis 16 may be coated with the matrix solution by spraying, dipping, deposition, or painting the polymer solution onto the prosthesis. Usually, the polymer is finely sprayed on the prosthesis while the prosthesis is rotating on a mandrel. A thickness of the matrix coating may be controlled by a time period of spraying and a speed of rotation of the mandrel. The thickness of the matrix coating is typically in a range from 0.01 micron to 100 microns, preferably in a range from 0.1 micron to 10 microns. Once the prosthesis has been coated with the substance/matrix, the stent may be placed in a vacuum or oven to complete evaporation of the solvent.

For example, a stainless steel Duraflex™ stent, having dimensions of 3.0 mm×14 mm is sprayed with a solution of 25 mg/ml mycophenolic acid (sold commercially by Sigma Chemicals) in a 100% ethanol or methanol solvent. The stent is dried and the ethanol is evaporated leaving the substance on a stent surface. A 75:25 PLLA/PCL copolymer (sold commercially by Polysciences) is prepared in 1,4 Dioxane (sold commercially by Aldrich Chemicals). The substance loaded stent is loaded on a mandrel rotating at 200 rpm and a spray gun (sold commercially by Binks Manufacturing) dispenses the copolymer solution in a fine spray on to the substance loaded stent as it rotates for a 10–30 second period. The stent is then placed in a oven at 25–35° C. up to 24 hours to complete evaporation of the solvent.

In a further embodiment, the means for releasing the substance may comprise a reservoir on or within the scaffold holding the substance (as shown in FIG. 9) and an external energy source for directing energy at the prosthesis after implantation to effect release of the substance. A matrix may be formed over the reservoir to contain the substance within the reservoir. Alternatively, the means for releasing the substance may comprise a matrix formed over at least a portion of the scaffold (as shown in FIGS. 4–6), wherein the substance is disposed under or within the matrix, and an external energy source for directing energy at the prosthesis after implantation to effect release of the substance. Suitable external energy source include ultrasound, magnetic resonance imaging, magnetic field, radio frequency, temperature change, electromagnetic, x-ray, radiation, heat, gamma, and microwave.

For example, an ultrasound external energy source may be used having a frequency in a range from 20 kHz to 100 MHz, preferably in a range from 0.1 MHz to 20 MHz, and an intensity level in a range from 0.05 W/cm$^2$ to 10 W/cm$^2$, preferably in a range from 0.5 W/cm to 5 W/cm . The ultrasound energy should be directed at the prosthesis 16 from a distance in a range from 1 mm to 30 cm, preferably in a range from 1 cm to 20 cm. The ultrasound may be continuously applied or pulsed, for a time period in a range from 5 sec to 30 minutes, preferably in a range from 1 minute to 15 minutes. The temperature of the delivery prosthesis 16 during this period will be in a range from 37° C. to 48° C. The ultrasound may be used to increase a porosity of the prosthesis 16, thereby allowing release of the substance 22 from the prosthesis 16.

Figure 10:
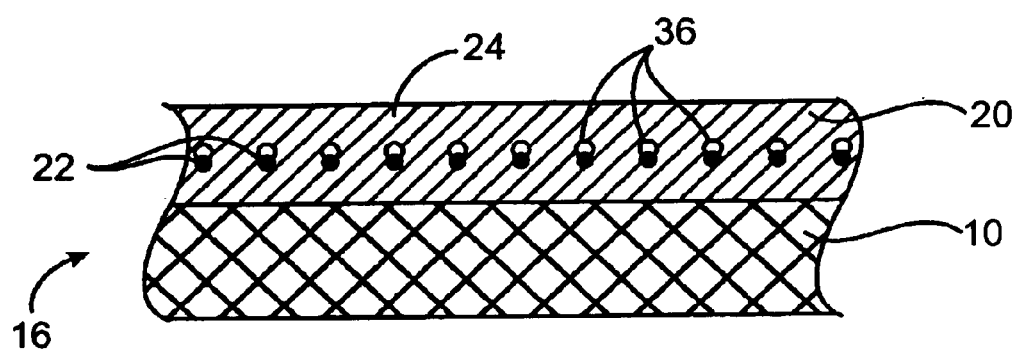
FIG. 10 is a partial cross-sectional view of a delivery prosthesis having magnetic releasing means.

In yet another embodiment, as depicted in FIG. 10, means for releasing the substance comprises magnetic particles 36 coupled to the substance 22 and a magnetic source for directing a magnetic field at the prosthesis 16 after implantation to effect release of the substance 22. Optionally, the means for releasing the substance may comprise magnetic particles 26 coupled to a matrix 20 formed over the scaffold 10 and a magnetic source for directing a magnetic field at the prosthesis 16 after implantation to effect release of the substance 22. The substance 22 may be disposed under (FIGS. 5 and 6) or within the matrix 20 (FIG. 10). The magnetic particles 36 may be formed from magnetic beads and will typically have a size in a range from 1 nm to 100 nm. The magnetic source exposes the prosthesis 16 to its magnetic field at an intensity typically in the range from 0.01T to 2T, which will activate the magnetic particles 36, and thereby effect release of the substance from the prosthesis.

Figure 11:
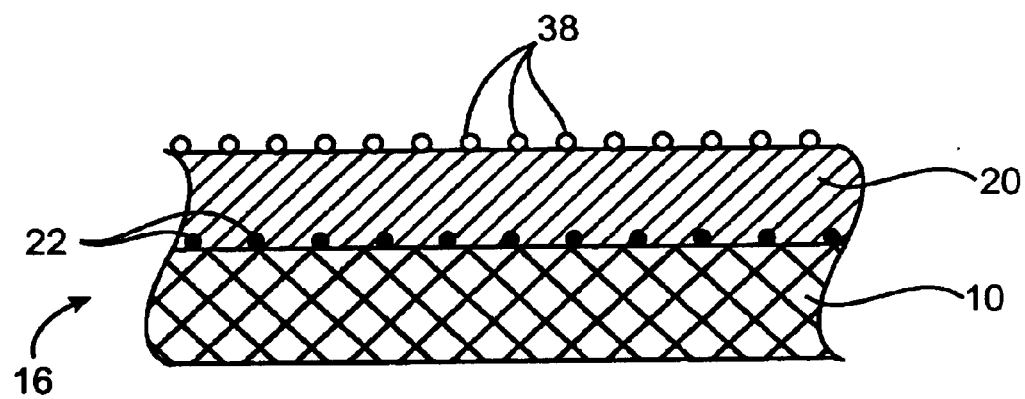
FIG. 11 is a partial cross-sectional view of a delivery prosthesis with cellular growth.

Referring now to FIG. 11, improved methods for delivering a pharmacological agent to an artery are illustrated. The method is of the type where a prosthesis 16 is implanted in the artery 18 and the prosthesis 16 releases the pharmacological agent 22. The improvement comprises implanting a prosthesis 16 that is programmed to begin substantial release of the pharmacological agent 22 beginning after growth of at least one layer of cells 38 over a part of the prosthesis. The cells 38 will typically comprise inflammation, smooth muscle, or endothelial cells, indicating the onset of restenosis.

Figure 12A:
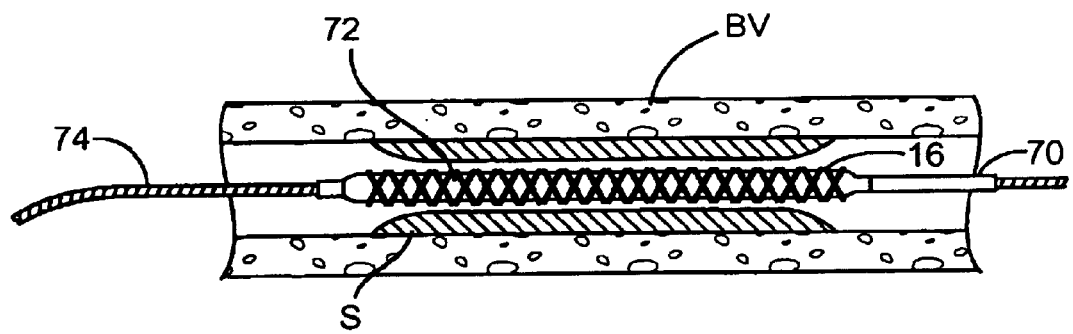
FIGS. 12A–12C illustrates a method for positioning a delivery prosthesis in a blood vessel in order to deliver a substance therein.
Figure 12B:
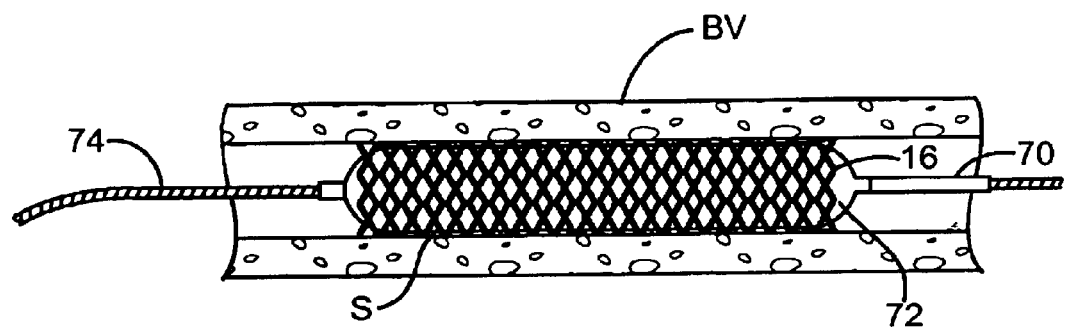
Figure 12C:
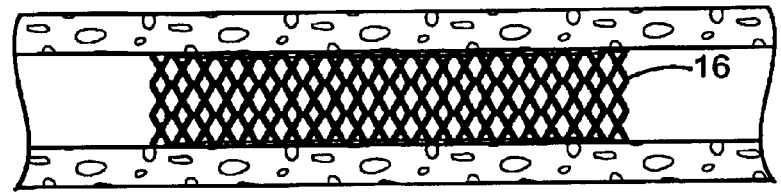

Referring now to FIGS. 12A–12C, a method for positioning the delivery prosthesis 16 in a body lumen in order to deliver a substance 22 therein will be described. As shown in FIG. 12A, a balloon dilation catheter 70 will typically be used to deliver the prosthesis 16 to a region of stenosis S in a blood vessel BV. The prosthesis 16 is initially carried in its radially collapsed diameter configuration on an deflated balloon 72 of the balloon catheter 70. The balloon catheter is typically introduced over a guidewire 74 under fluoroscopic guidance. The catheters and guidewires may be introduced through conventional access sites to the vascular system, such as through the femoral artery, or brachial, subclavian or radial arteries, for access to the coronary arteries. After the delivery prosthesis 16 is properly positioned within the region of stenosis (FIG. 12A), the balloon 72 will be inflated to radially expand the prosthesis 16 (FIG. 12B) within the stenotic region. The balloon 72 may then be deflated, and the catheter 70 may be withdrawn over the guidewire 74. After removal of the guidewire 74, the expanded prosthesis 16 will be left in place, as illustrated in FIG. 12C, to provide luminal substance delivery as described above to inhibit restenotic effects.

In general, it will be possible to combine elements of the differing prostheses and treatment methods as described above. For example, a prosthesis having reservoir means for releasing the substance as illustrated in FIG. 9 may further incorporate a rate limiting barrier as illustrated in FIG. 8. Additionally, methods of the present invention may combine balloon angioplasty and/or other interventional treatments to resolve a stenotic site with the presently described luminal substance delivery treatments.

Although certain preferred embodiments and methods have been disclosed herein, it will be apparent from the foregoing disclosure to those skilled in the art that variations and modifications of such embodiments and methods may be made without departing from the true spirit and scope of the invention. Therefore, the above description should not be taken as limiting the scope of the invention which is defined by the appended claims.

What is claimed is:

1. A method for luminal substance delivery, said method comprising:

providing a luminal prosthesis incorporating and/or coupled to a substance, wherein the prosthesis comprises a rate limiting barrier; and implanting the prosthesis in a body lumen so that the substance is released from the prosthesis at multiple rates including an initial rate and at least one subsequent rate which is substantially higher than the initial rate and begins after an appreciable preselected time period.

2. A method as in claim 1, wherein the barrier has a sufficient thickness to allow diffusion of the substance through the barrier.

3. A method as in any of claims 1–2, wherein the at least one subsequent rate begins within a time period ranging from 4 hours to 24 weeks in a vascular environment.

4. A method as in any of claim 3, wherein the at least one subsequent rate begins within a time period of 1 day to 12 weeks in a vascular environment.

5. A method as in any of claim 3, wherein the at least one subsequent rate begins within a time period of 2 days to 8 weeks in a vascular environment.

6. A method as in claim 3, wherein the at least one subsequent rate begins within a time period of 3 days to 50 days in a vascular environment.

7. A method as in any one of claims 1–2, wherein the substance comprises at least one agent selected from the group consisting of immunosuppressant agent, anti-inflammatory agent, anti-proliferative agent, anti-migratory agent, anti-fibrotic agent, anti-thrombotic agent, anti-platelet agent, and IIb/IIIa agent.

8. A method as in claim 1, further comprising directing energy at the prosthesis to effect release of the substance from the prosthesis.

9. A method as in claim 8, wherein the energy is at least one of ultrasound, magnetic resonance imaging, magnetic field, radio frequency, temperature change, electromagnetic, x-ray, radiation, heat, gamma, or microwave.

10. A method as in claim 1, wherein the prosthesis incorporates the substance by coating, spraying, dipping, deposition, or painting the substance on the prosthesis.

11. A method as in claim 1, wherein the substance is incorporated in a reservoir in or on a scaffold containing the substance.

12. A method as in claim 1, wherein the prosthesis incorporates magnetic particles coupled to the substance and further comprising the step of directing a magnetic field at the prosthesis to effect release of the substance from the prosthesis.

13. A method as in claim 1, wherein the initial rate is in a range between 0 $\mu$g/day to 50 $\mu$g/day.

14. A method as in claim 13, wherein the initial rate is in a range between 5 $\mu$g/day to 30 $\mu$g/day.

15. A method as in claim 1, wherein the at least one subsequent rate is in a range between 5 $\mu$g/day to 200 $\mu$g/day.

16. A method as in claim 15, wherein the at least one subsequent rate is in a range between 10 $\mu$g/day to 100 $\mu$g/day.

* * * * *